United States Patent
Wang et al.

(10) Patent No.: US 9,617,214 B2
(45) Date of Patent: Apr. 11, 2017

(54) COMPOUNDS FOR COGNITIVE ENHANCEMENT AND METHODS OF USE THEREOF

(71) Applicants: The Translational Genomics Research Institute, Phoenix, AZ (US); Translational Drug Development, LLC, Scottsdale, AZ (US)

(72) Inventors: Tong Wang, Phoenix, AZ (US); Travis Dunckley, Phoenix, AZ (US); Matthew Huentelman, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 15/034,131

(22) PCT Filed: Nov. 10, 2014

(86) PCT No.: PCT/US2014/064868
§ 371 (c)(1),
(2) Date: May 3, 2016

(87) PCT Pub. No.: WO2015/070170
PCT Pub. Date: May 14, 2015

(65) Prior Publication Data
US 2016/0272587 A1    Sep. 22, 2016

Related U.S. Application Data

(60) Provisional application No. 61/902,022, filed on Nov. 8, 2013.

(51) Int. Cl.
| | |
|---|---|
| A61K 45/06 | (2006.01) |
| C07D 213/56 | (2006.01) |
| C07D 405/12 | (2006.01) |
| A61K 31/4409 | (2006.01) |
| A61K 31/4433 | (2006.01) |
| A61K 31/4418 | (2006.01) |

(52) U.S. Cl.
CPC ........ *C07D 213/56* (2013.01); *A61K 31/4409* (2013.01); *A61K 31/4418* (2013.01); *A61K 31/4433* (2013.01); *A61K 45/06* (2013.01); *C07D 405/12* (2013.01)

(58) Field of Classification Search
CPC .... C07D 405/12; C07D 213/56; A61K 45/06; A61K 31/4433; A61K 31/4418; A61K 31/4409
See application file for complete search history.

(56) References Cited

U.S. PATENT DOCUMENTS

| | | |
|---|---|---|
| 2011/0150833 A1 | 6/2011 | Feng et al. |
| 2011/0237600 A1 | 9/2011 | Nikolich et al. |

FOREIGN PATENT DOCUMENTS

| | | | | |
|---|---|---|---|---|
| WO | WO 2009027392 A1 * | 3/2009 | ........... | C07D 213/56 |

OTHER PUBLICATIONS

A. Salminen et al., 371 Biochemical and Biophysical Research Communications, 587-590 (2008).*
Y. Liu et al., 1490 Brain Research, 43-51 (2013).*
L. Huang et al., 277 Neuroscience, 383-391 (2014).*
International Search Report and Written Opinion for PCT Application No. PCT/US2014/064868.
Feng et al. Discovery of Substituted 4-(Pyrazol-4-yl)-phenylbenzodioxane-2-carboxamides as Potent and Highly Selective Rho Kinase (ROCK-II) inhibitors, Journal of Medicinal Chemistry, 2008 vol. 51, pp. 6642-6645.
Davidowitz et al., Targeting Tau oligomers for therapeutic development for Alzheimer's disease and taupathies, Current Topics in Biotechnology, 2008 vol. 4, pp. 47-64.

* cited by examiner

*Primary Examiner* — Alexander R Pagano
(74) *Attorney, Agent, or Firm* — Rodney J. Fuller; Booth Udall Fuller, PLC

(57) ABSTRACT

The invention provides compounds that inhibit ROCK activity. In certain embodiments the compounds of the invention enhance cognitive function. The invention is also directed to pharmaceutical compositions that comprise ROCK inhibitors and to methods enhance cognitive function and reducing and/or treat cognitive function decline.

8 Claims, 6 Drawing Sheets

COMPOUNDS FOR COGNITIVE ENHANCEMENT AND METHODS OF USE THEREOF

RELATED APPLICATION DATA

This application is the national stage of International Patent Application No. PCT/US2014/064868, filed on Nov. 10, 2014, which claims the benefit of U.S. Provisional Application No. 61/902,022 filed Nov. 8, 2013, which is hereby incorporated by reference in its entirety.

STATEMENT REGARDING FEDERALLY SPONSORED RESEARCH

This invention was made with government support under NS059873, awarded by the National Institutes of Health. The government has certain rights in the invention.

FIELD OF THE INVENTION

The present invention is related to compositions and methods for enhancing cognitive functions. In some aspects, the methods and compositions can be used as a prophylactic measure and/or a treatment for cognition-associated diseases, wherein Rho-associate protein kinase (ROCK) is inhibited.

BACKGROUND OF THE INVENTION

Alzheimer's disease (AD) is the most common cause of disabling memory and thinking problems in older persons. According to one study, it afflicts about 10% of those over the age of 65 and almost half of those over the age of 85. According to another study, the prevalence of the disorder increases from 1% by the age of 60 years to 40% in nonagenarians. By 2050, the number of afflicted persons is projected to quadruple, leading to approximately 16 million patients and a cost of more than $750 billion per year in the United States alone. In the meantime, the disorder takes a devastating toll on patients and their families. Clinically, AD is characterized by gradual but progressive declines in memory, language skills, the ability to recognize objects or familiar faces, the ability to perform routine tasks, and judgment and reasoning. Associated features commonly include agitation, paranoid delusions, sleepiness, aggressive behaviors, and wandering. In its most severe form, patients may be confused, bed-ridden, unable to control their bladder or bowel functions, or swallow. With the contribution of other problems (e.g., inanition and infections), AD is considered the fourth leading cause of death in the United States.

To date, the FDA has only approved five drugs for the treatment of AD, and all of these treatments only temporarily alleviate symptoms such as cognitive decline and memory loss without affecting changes in neurophysiology. AD pathology includes amyloid plaques and neurofibrillary tangles (NFT), which are made of Aβ(1-42) deposits and hyperphosphorylated tau, respectively. Thus there is a need for therapeutics that decreases amyloid plaque formations, decreases NFT formation, or increases cognitive function.

SUMMARY OF THE INVENTION

The invention is directed to broadly to new ROCK inhibitors and to method of treating or reducing ***a compound, or a pharmaceutically acceptable salt or solvate thereof, of the formula selected from the group consisting of:

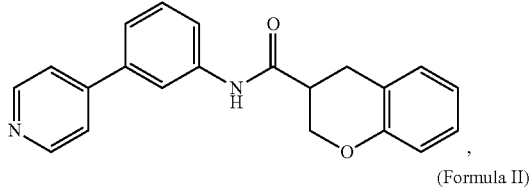

(Formula I)

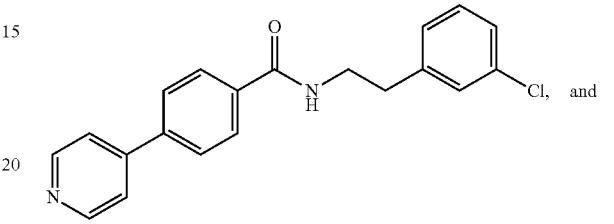

(Formula II)

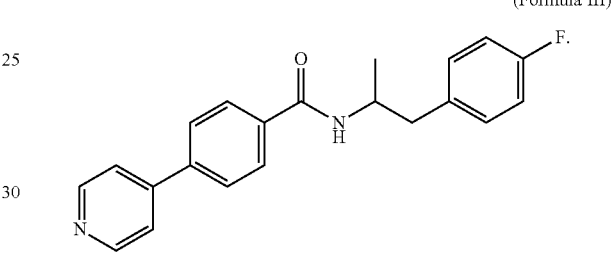

(Formula III)

Other embodiments of the invention provide a pharmaceutical composition comprising the compound, or a pharmaceutically acceptable salt or solvate thereof, of the formula selected from the group consisting of Formulas I-III. The pharmaceutical composition may further comprise a second effective compound of a distinct chemical formula from the first compound. All pharmaceutical compositions of the invention may additionally comprise a pharmaceutically acceptable carrier.

In some embodiments, the invention the invention is directed to a method of enhancing cognitive function or preventing or treating cognitive function decline. The method generally includes the step of administering a therapeutically effective amount of one or more compounds to a subject. The enhanced cognitive function is memory, for example, short-term memory or spatial reference memory. Furthermore, the compound is generally administered in a pharmaceutical composition. For the methods disclosed herein the subject is an animal, and typically a human.

In other embodiments the invention is directed to a method a subject with Alzheimer's disease (AD) in an amount sufficient to treat AD in the subject.

The present invention is also directed to method of providing neuroprotection in a subject by administering to the subject one or more compounds of the invention in an amount sufficient to provide neuroprotection.

Some embodiments of the invention provide a method of treating taupathy in a subject, such as an animal, by administering a therapeutically effective amount of the above compound to the subject. In some aspects, the invention provides a method of decreasing a ratio of phosphorylated tau protein to total tau protein in the subject. In some aspects, the phosphorylated tau protein comprises a phosphate group at Serine 396. In some aspects, the invention provides a method of inhibiting the activity of Rho-associate protein kinase in the subject, In some implementations of the invention, the animal may be a human. The subject may have no discernible symptoms of any form of a cognition-associated disease, such as a healthy human, or the subject may have cognitive function decline or impairment, for example, stemming from a cognition-associated disease, such as AD or dementia.

Additional objectives, advantages and novel features will be set forth in the description which follows or will become apparent to those skilled in the art upon examination of the drawings and detailed description which follows.

Figure 1:
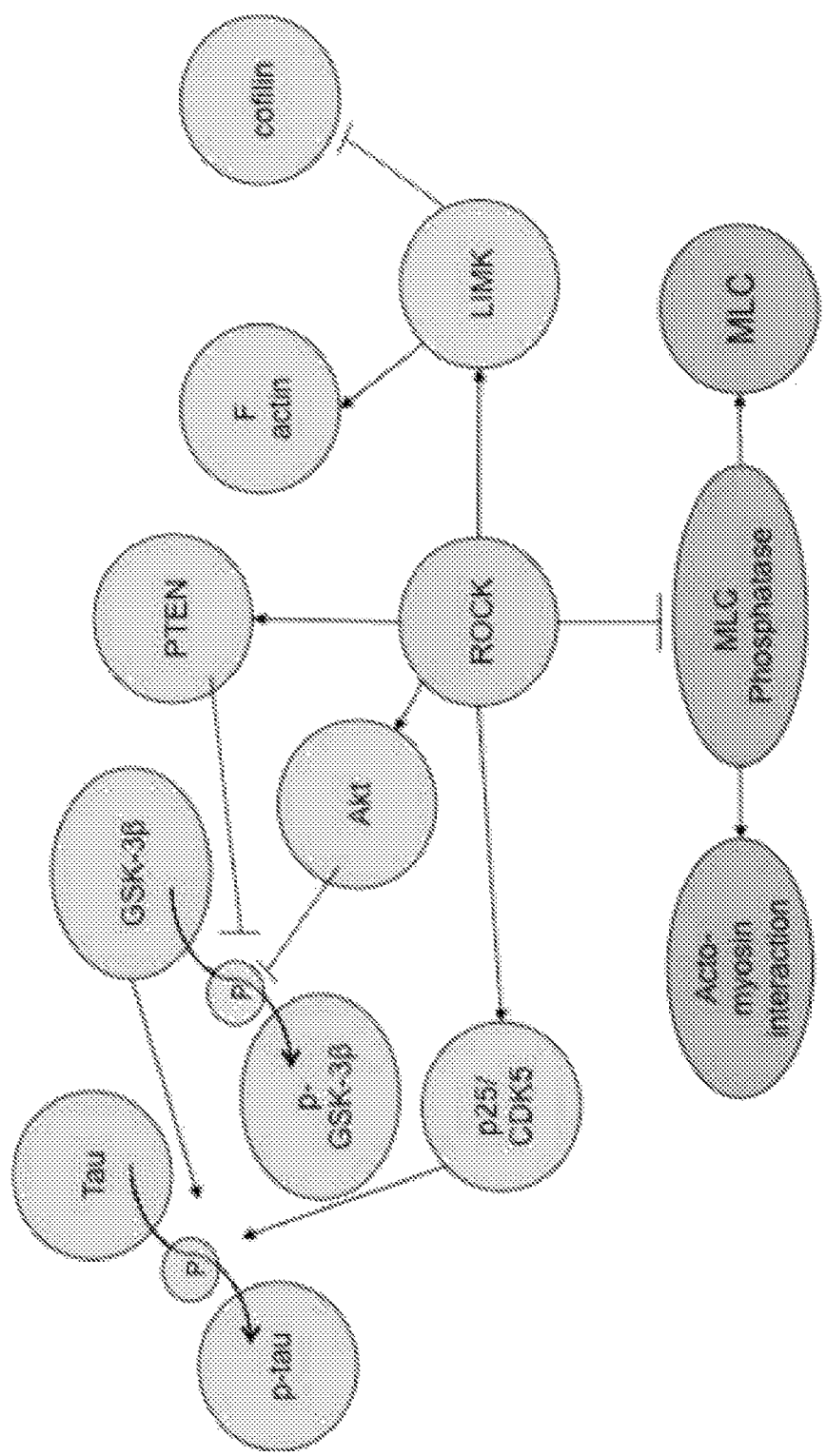
FIG. 1 is a simplified schematic of the ROCK-mediated signaling pathway.

The headings used in the figures should not be interpreted to limit the scope of the claims.

DETAILED DESCRIPTION

As used herein, "Rho-associate protein kinase," "Rho-associated, coiled-coil-containing protein kinase," "Rho kinase," or "ROCK" refer to a family of serine/threonine kinases that are activated via interaction with Rho GTPases. ROCK members have a molecular mass of about 160 kDa, each kinase contains a catalytic kinase domain at the amino terminus, followed by a central coiled-coil domain including a Rho-binding domain (RBD), and a carboxyl-terminal pleckstrin-homoslogy (PH) domain with an internal cysteine-rich (CR) domain. ROCK has auto-inhibitory activity. In the inactive form, the carboxyl terminal PH domain and RBD of ROCK interact with the kinase domain, which forms an auto-inhibitory loop. The kinase domain contains the conserved motifs associated with serine/threonine protein kinases.

As used herein, "cognition," "cognitive," or "cognitive function" refers to mental processes that include attention, memory, producing and understanding language, learning, reasoning, problem solving, decision-making, and other related processes.

As used herein, "neuroprotection" refers to the protection of central nervous system cells from cellular change such that cognitive functions are impaired as a result of the change.

As used herein, "total tau protein" refers to the detectable concentration of phosphorylated and non-phosphorylated tau protein.

As used herein, "taupathy" or the plural form "taupathies" refers to any disease or pathological condition that is associated with a deviation from acceptable equilibrium in the ratio of phosphorylated tau (p-tau) protein to total tau protein. "Acceptable equilibrium" refers to a ratio of p-tau protein to total tau protein in a subject that results in a generally non-diseased state.

The invention relates to compounds, compositions, kits, and methods for the enhancement of cognitive function. The enhancement of cognitive function may be a result of preventing or treating cognitive function decline, thus some embodiments of the invention relate to compounds, compositions, kits, and methods for preventing or treating cognitive function decline.

In some embodiments, cognitive function is enhanced through modulating ROCK. As a non-limiting example, the enhancement of cognitive function may be achieved through inhibiting the activity of ROCK. Experiments with ROCK inhibitors, for example, Fasudil (5-(1,4-diazepan-1-ylsulfonyl)isoquinoline) and Y27632 (4-(1-aminoethyl)-N-pyridin-4-yl-cyclohexane-1-carboxamide), present more direct evidence of the correlation between ROCK and cognitive function. Administration of Fasudil can enhance memory and improve the prognosis of AD patients. In age rats, administration of Fasudil increased learning and memory. When Fasudil was applied to H4-tau cells, a neuronal cell line transformed to overexpress human tau protein, the treatment decreased the ratio of p-tau protein to total tau protein in H4-tau cells. In a mouse model of AD, administration of Y27632 preferentially lowered brain levels of Aβ42. In another study, Y27632 decreased the hyperphosphorylation of the tau protein due to ischemia and increased memory and learning of these rats, but administration of the compound in sham rats, where there was no hyperphosphorylation of the tau protein, decreased memory and learning.

ROCK is activated via interaction with Rho GTPases. Rho GTPase family proteins, which include Rho, Rac1, and Cdc42, control a wide variety of cellular processes such as cell adhesion, motility, proliferation, differentiation and apoptosis. The ROCK family of proteins contains two members: ROCK1 (UniProtKB/Swiss-Prot Accession No: Q13464) and ROCK2 (UniProtKB/Swiss-Prot Accession No: O75116). ROCK1 and ROCK2 share 65% overall identity and 92% identity in the kinase domain. The ROCK1 gene locus is at chromosome 18q11.1, and the ROCK2 gene locus is at chromosome 2p24. Whereas ROCK2 is found more often in the brain, ROCK1 is mostly found in the periphery.

The majority of ROCK substrates have been identified from cell culture experiments. In most cases, only ROCK2 has been tested. Because ROCK1 and ROCK2 share 92% identity in the kinase domain, it has been assumed that they share the same substrates. However, ROCK1 and ROCK2 may have different targets as only ROCK1, not ROCK2, binds to and phosphorylates RhoE. Most of the known ROCK substrates are cellular proteins associated with the regulation of the actin cytoskeleton. Referring to FIG. 1, ROCK inhibits myosin light chain (MLC) phosphatase, which activates MLC and acto-myosin interactions. ROCK also activates LIM kinase (LIMK). Both MLC and LIMK cause neuronal cell death and synaptic loss during excitotoxicity. ROCK also increases PTEN and AKT activity, thereby reducing glycogen synthase kinase-3β (GSK-3β) phosphorylation. Additionally, ROCK increases p25 activity of CDK5. Both non-phosphorylated GSK-3β and p25 activity of CDK5 increase the phosphorylation of tau. In particular, phosphorylation of tau at Serine 396 decreases the ability of tau to bind to microtubules, which at least partially contributes to the tau-related pathology (i.e., in forming NFT) in AD. Thus in some embodiments of the invention, enhancement of cognitive function may be achieved by decreasing the ratio of p-tau protein, for example phosphorylation of p-tau at Serine 396, to total tau protein.

ROCK has also been implicated in formation of amyloid plaque, as ROCK inhibitors were shown to decrease Aβ levels in vitro. Accordingly, in some embodiments of the invention, enhancement of cognitive function may be achieved by decreasing the amount of amyloid plaques, for example, by decreasing the levels of Aβ.

The Compound and the Pharmaceutical Composition

Compounds of the invention are described in Table 1 and include their pharmaceutically acceptable salts of solvates. These compounds are ROCK inhibitors.

TABLE 1

| ID | Structure | Formula Weight |
|---|---|---|
| T303 (Formula I) | 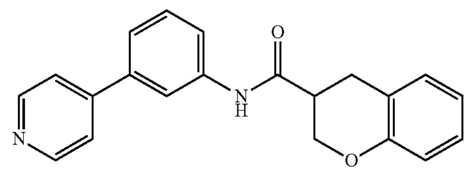 [SMILES: O=C(Nc1cccc(-c2ccncc2)c1)C1COc2ccccc2C1] | 330.28 g/mol |
| T343 (Formula II) | 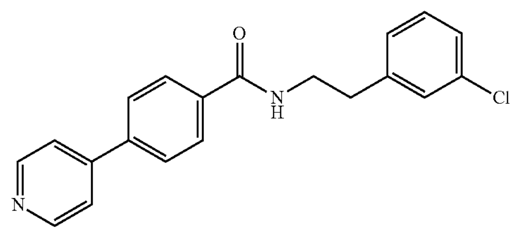 [SMILES: O=C(NCCc1cccc(Cl)c1)c1ccc(-c2ccncc2)cc1] | 338.81 g/mol |
| T350 (Formula III) | 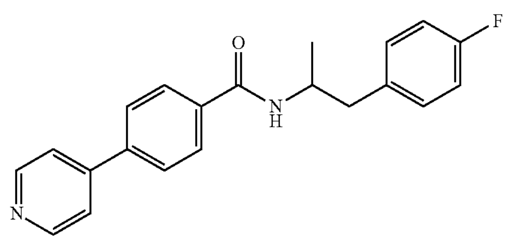 [SMILES: CC(Cc1ccc(F)cc1)NC(=O)c1ccc(-c2ccncc2)cc1] | 334.39 g/mol |
| T299 (Formula IV) | 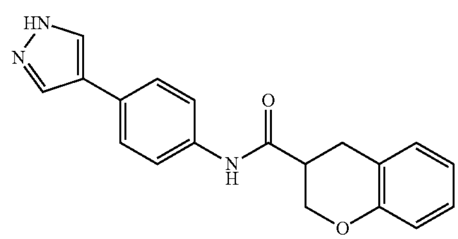 [SMILES: O=C(Nc1ccc(-c2cn[nH]c2)cc1)C1COc2ccccc2C1] | 319.36 g/mol |
| T306 (Formula V) | 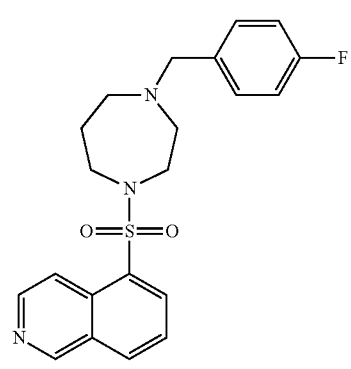 [SMILES: O=S(=O)(c1cccc2cnccc12)N1CCCN(Cc2ccc(F)cc2)CC1] | 399.48 g/mol |

TABLE 1-continued

| ID | Structure | Formula Weight |
|---|---|---|
| T347 (Formula VI) | 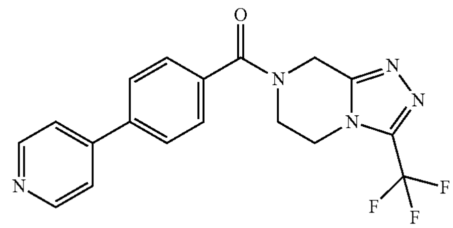 [SMILES: O=C(c1ccc(-c2ccncc2)cc1)N1CCn2c(nnc2C(F)(F)F)C1] | 373.33 g/mol |
| T349 (Formula VII) | 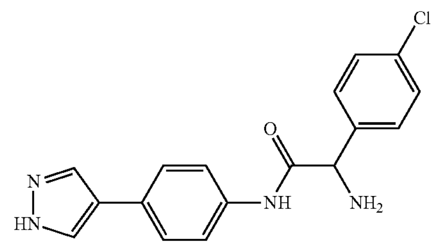 [SMILES: NC(C(=O)Nc1ccc(-c2cn[nH]c2)cc1)c1ccc(Cl)cc1] | 326.78 g/mol |
| T355 (Formula VIII) | 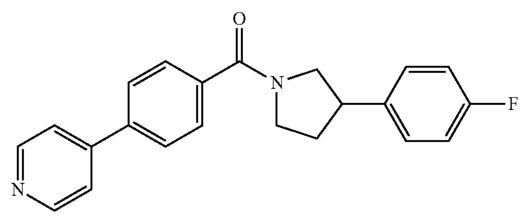 [SMILES: O=C(c1ccc(-c2ccncc2)cc1)N1CCC(c2ccc(F)cc2)C1] | 346.4 g/mol |
| T300 | 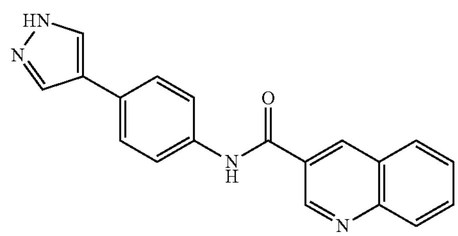 [SMILES: O=C(Nc1ccc(-c2cn[nH]c2)cc1)c1cnc2ccccc2c1] | 314.34 g/mol |
| T301 | 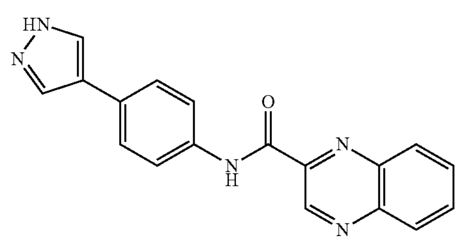 [SMILES: O=C(Nc1ccc(-c2cn[nH]c2)cc1)c1cnc2ccccc2n1] | 315.33 g/mol |
| T302 | 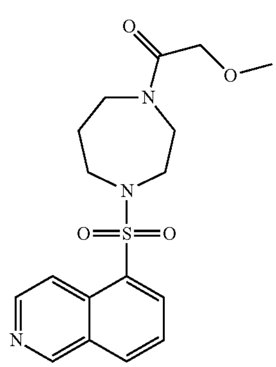 [SMILES: COCC(=O)N1CCCN(S(=O)(=O)c2cccc3cnccc23)CC1] | 363.43 g/mol |

TABLE 1-continued
| ID | Structure | Formula Weight |
| --- | --- | --- |
| T304 | 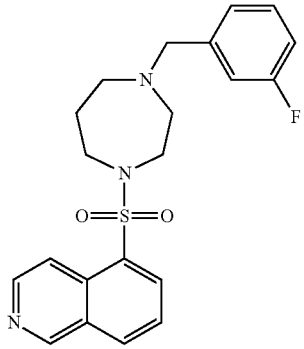 [SMILES: O=S(=O)(c1cccc2cnccc12)N1CCCN(Cc2cccc(F)c2)CC1] | 399.48 g/mol |
| T305 | 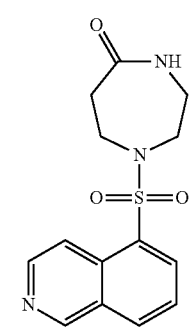 [SMILES: O=C1CCN(S(=O)(=O)c2cccc3cnccc23)CCN1] | 305.35 g/mol |
| T307 | 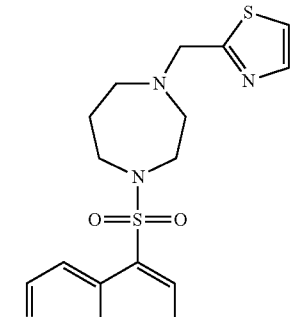 | 388.51 g/mol |
| T308 | 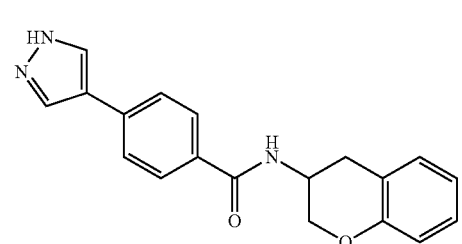 | 319.36 g/mol |
| T309 | 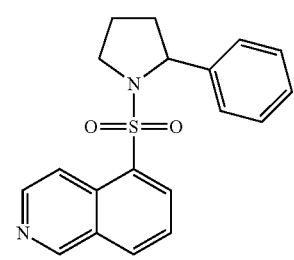 [SMILES: O=S(=O)(c1cccc2cnccc12)N1CCCC1c1ccccc1] | 338.42 g/mol |

TABLE 1-continued

| ID | Structure | Formula Weight |
| --- | --- | --- |
| T310 | 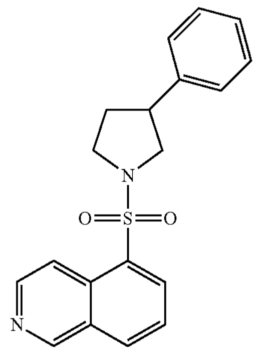 [SMILES: O=S(=O)(c1cccc2cnccc12)N1CCC(c2ccccc2)C1] | 338.42 g/mol |
| T311 | 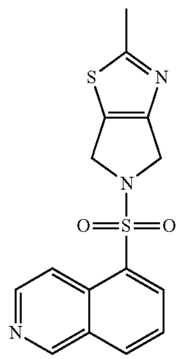 [SMILES: Cc1nc2c(s1)CN(S(=O)(=O)c1cccc3cnccc13)C2] | 331.41 g/mol |
| T312 | 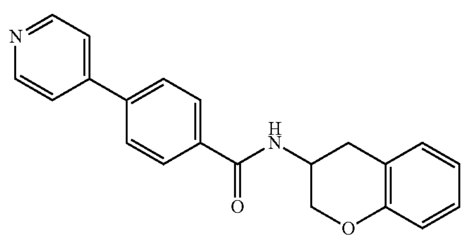 [SMILES: O=C(NC1COc2ccccc2C1)c1ccc(-c2ccncc2)cc1] | 330.38 g/mol |
| T334 | 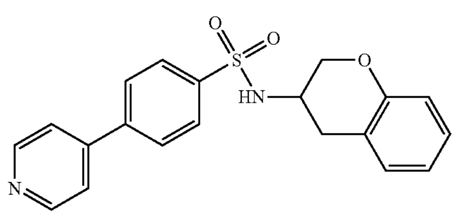 [SMILES: O=S(=O)(NC1COc2ccccc2C1)c1ccc(-c2ccncc2)cc1] | 366.43 g/mol |
| T335 | 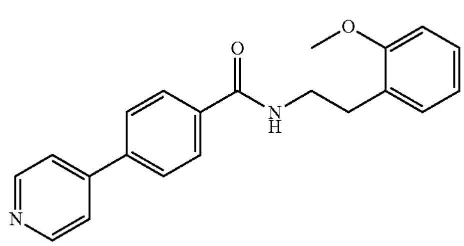 [SMILES: COc1ccccc1CCNC(=O)c1ccc(-c2ccncc2)cc1] | 332.4 g/mol |

TABLE 1-continued
| ID | Structure | Formula Weight |
|---|---|---|
| T336 | 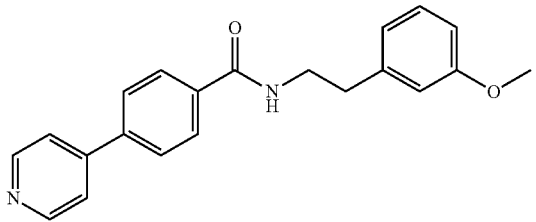 [SMILES: COc1cccc(CCNC(=O)c2ccc(-c3ccncc3)cc2)c1] | 332.4 g/mol |
| T337 | 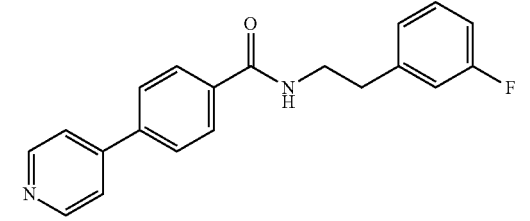 [SMILES: O=C(NCCc1cccc(F)c1)c1ccc(-c2ccncc2)cc1] | 320.36 g/mol |
| T338 | 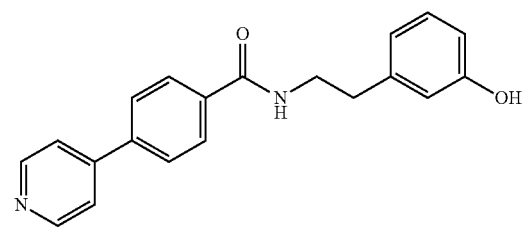 [SMILES: O=C(NCCc1cccc(O)c1)c1ccc(-c2ccncc2)cc1] | 318.37 g/mol |
| T339 | 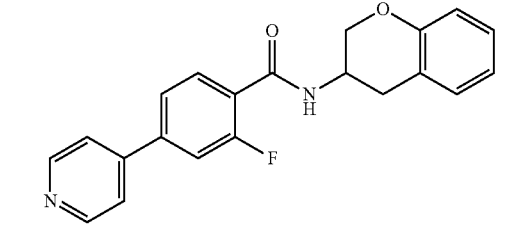 [SMILES: O=C(NC1COc2ccccc2C1)c1ccc(-c2ccncc2)cc1F] | 348.37 g/mol |
| T340 | 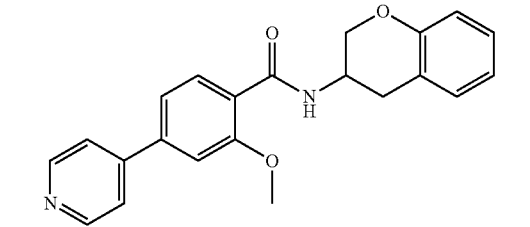 [SMILES: COc1cc(-c2ccncc2)ccc1C(=O)NC1COc2ccccc2C1] | 360.41 g/mol |
| T341 | 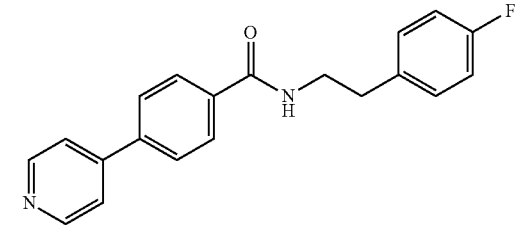 [SMILES: O=C(NCCc1ccc(F)cc1)c1ccc(-c2ccncc2)cc1] | 320.36 g/mol |

TABLE 1-continued
| ID | Structure | Formula Weight |
|---|---|---|
| T342 | 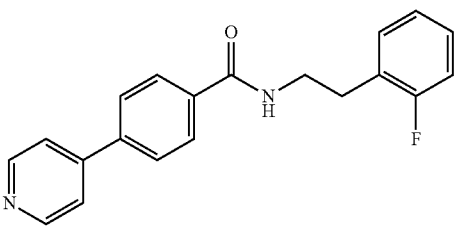 [SMILES: O=C(NCCc1ccccc1F)c1ccc(-c2ccncc2)cc1] | 320.36 g/mol |
| T344 | 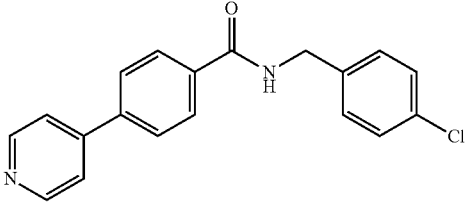 [SMILES: O=C(NCc1ccc(Cl)cc1)c1ccc(-c2ccncc2)cc1] | 322.79 g/mol |
| T345 | 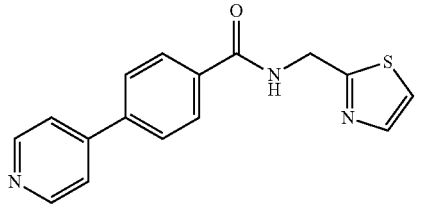 [SMILES: O=C(NCc1nccs1)c1ccc(-c2ccncc2)cc1] | 295.36 g/mol |
| T346 | 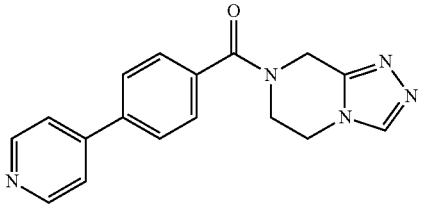 [SMILES: O=C(c1ccc(-c2ccncc2)cc1)N1CCn2cnnc2C1] | 305.33 g/mol |
| T348 | 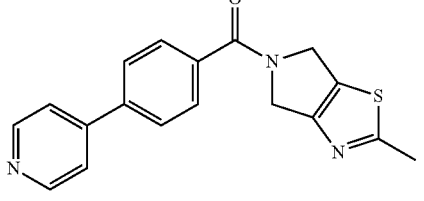 | 321.4 g/mol |
| T351 | 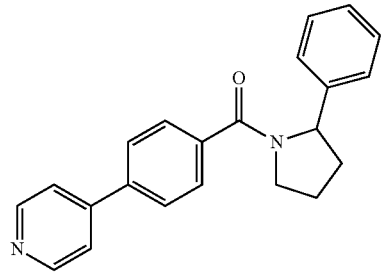 [SMILES: O=C(c1ccc(-c2ccncc2)cc1)N1CCCC1c1ccccc1] | 328.41 g/mol |
| T352 | 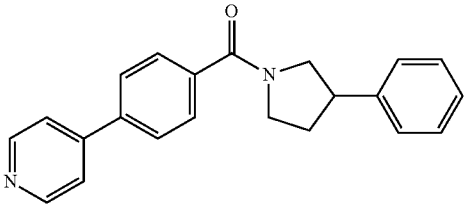 [SMILES: O=C(c1ccc(-c2ccncc2)cc1)N1CCC(c2ccccc2)C1] | 328.41 g/mol |

TABLE 1-continued

| ID | Structure | Formula Weight |
|---|---|---|
| T353 | 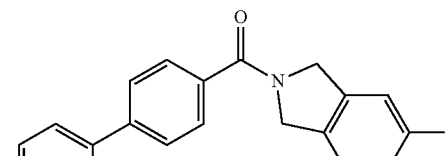 | 318.34 g/mol |
| T354 | 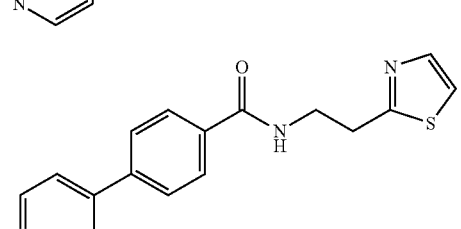 | 309.39 g/mol |

In some embodiments of the invention, the compounds decrease the ratio of p-tau protein to total tau protein. Examples of preferred compounds that decrease the ration of p-tau protein to total tau protein include compounds of Formulas I to III.

The disclosed compounds and their intermediates may exist in different tautomeric forms. Tautomers include any structural isomers of different energies that have a low energy barrier to interconversion. One example is proton tautomers (prototropic tautomers.) In this example, the interconversions occur via the migration of a proton. Examples of prototropic tautomers include, but are not limited to keto-enol and imine-enamine isomerizations. In another example illustrated graphically below, proton migration between the 1-position and 3-position nitrogen atoms of the benzimidazole ring may occur. As a result, Formulas Ia and Ib are tautomeric forms of each other:

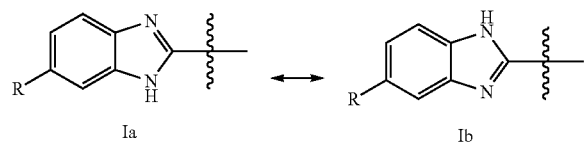

The disclosed compound further encompasses any other physiochemical or stereochemical form that the disclosed compound may assume. Such forms include diastereomers, racemates, isolated enantiomers, hydrated forms, solvated forms, or any other known or yet to be disclosed crystalline, polymorphic crystalline, or amorphous form. Amorphous forms lack a distinguishable crystal lattice and therefore lack an orderly arrangement of structural units. Many pharmaceutical compounds have amorphous forms. Methods of generating such chemical forms will be well known by one with skill in the art.

Pharmaceutical compositions of the invention comprise one or more compounds of Formula I-VII or a pharmaceutically acceptable salt or solvate thereof. Pharmaceutical compositions that include the disclosed compound may be prepared using methodology well known in the pharmaceutical art. Some embodiments of the pharmaceutical composition may comprise a second effective compound of a distinct chemical formula from the compound of Formula I, II, or III. This second effective compound may have the same or a similar molecular target as the target or it may act upstream or downstream of the molecular target of the disclosed compound with regard to one or more biochemical pathways, including pathways associated with ROCK.

Pharmaceutical compositions may take any physical form necessary depending on a number of factors including the desired method of administration and the physicochemical and stereochemical form taken by the compound or pharmaceutically acceptable salts of the compound. Such physical forms include a solid, liquid, gas, sol, gel, aerosol, or any other physical form now known or yet to be disclosed. Non-limiting examples are solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, or elixirs. Additional examples of suitable pharmaceutical carriers and formulations are well known in the art. The physical form of the invention may affect the route of administration and one skilled in the art would know to choose a route of administration that takes into consideration both the physical form of the compound and the disorder to be treated.

In some embodiments, pharmaceutical compositions including the disclosed compound include materials capable of modifying the physical form of a dosage unit. In one non-limiting example, the composition includes a material that forms a coating that contains the compound. Materials that may be used in a coating include, for example, sugar, shellac, gelatin, or any other inert coating agent.

Aerosol forms of the pharmaceutical compositions of the invention encompass a variety of systems, including colloids and pressurized packages. Delivery of a composition in this form may include propulsion of a pharmaceutical composition including the disclosed compound through use of liquefied gas or other compressed gas or by a suitable pump system. Aerosols may be delivered in single-phase, bi-phasic, or multi-phasic systems.

Solvate form of the pharmaceutical composition of the invention, may, for example, be produced by the dissolution of the disclosed compound in a pharmaceutically acceptable solvent. Pharmaceutically acceptable solvents include any mixtures of one or more solvents. Such solvents may include pyridine, chloroform, propan-1-ol, ethyl oleate, ethyl lactate, ethylene oxide, water, ethanol, and any other solvent that delivers a sufficient quantity of the disclosed compound to treat the indicated condition.

Pharmaceutical compositions comprising the compound of Formula I or pharmaceutically acceptable salt or solvate thereof may further comprise at least one pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, and oils (including petroleum, animal, vegetable or synthetic oils.) Such carriers include particulates such as a tablet or powder, liquids such as oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intramsal, intracerebral, iratraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include the use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle. Additional examples of suitable modes of administration are well known in the art.

A pharmaceutical composition formulated to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions may be prepared in a form that facilitates topical or transdermal administration. Such preparations may be in the form of a solution, emulsion, ointment, gel base, transdermal patch or iontophoresis device. Examples of bases used in such compositions include opetrolatum, lanolin, polyethylene glycols, beeswax, mineral oil, diluents such as water and alcohol, and emulsifiers and stabilizers, thickening agents, or any other suitable base now known or yet to be disclosed.

Pharmaceutical compositions may be administered prior to, concurrently with, or after administration of additional or second pharmaceutical compositions that may or may not include the compound. Concurrent administration means compositions are administered within about one minute of each other. If not administered concurrently, the additional or second pharmaceutical compositions may be administered a period of one or more minutes, hours, days, weeks, or months before or after the pharmaceutical composition that includes the currently disclosed compound. Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration. Cycling therapy may be used, for example, to reduce the development of resistance to one or more of the compositions, to avoid or reduce the side effects of one or more of the compositions, and/or to improve the efficacy of the treatment.

The addition of a therapeutically effective amount of the disclosed compound encompasses any method of dosing of a compound. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A dosing regimen including the regularity of and mode of administration will be dependent on any of a number of factors including but not limited to the subject being treated; the severity of the condition; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Determination of a therapeutically effective amount of the disclosed compound is within the capability of those skilled in the art, especially in light of the detailed disclosure provided herein. The effective amount of a pharmaceutical composition used to affect a particular purpose as well as its toxicity, excretion, and overall tolerance may be determined in vitro, or in vivo, by pharmaceutical and toxicological procedures either known now by those skilled in the art or by any similar method yet to be disclosed. One example is the in vitro determination of the $IC_{50}$ (half maximal inhibitory concentration) of the pharmaceutical composition in cell lines or target molecules. Another example is the in vivo determination of the $LD_{50}$ (lethal dose causing death in 50% of the tested animals) of the pharmaceutical composition. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who can use data obtained from any tests in making that determination. Determination of an effective amount of disclosed compound for administration also includes the determination of an effective therapeutic amount and a pharmaceutically acceptable dose, including the formulation of an effective dose range for use in vivo, including in humans.

The invention further encompasses kits that facilitate the administration of the disclosed compound to a diseased entity. An example of such a kit includes one or more unit dosages of the compound. The unit dosage would be enclosed in a preferably sterile container and would be comprised of the disclosed compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage. In another aspect, the kit may include one or more additional compounds for administration and administration instructions therefor.

Uses

The invention provides methods of enhancing cognitive function. Methods of the invention involve the administration of a therapeutically effective amount of the compound of Formula I or a pharmaceutical composition comprising the compound of Formula I and/or a pharmaceutically acceptable salt thereof to a subject. The subject includes but is not limited to an animal, including a mammal (in particular, a human). In some implementations, the subject that receives the composition may be suffering from cognitive decline or impairment, such as those stemming from cognition-associated diseases, such as Alzheimer's disease (AD) or dementia. In other implementations, the subject that receives the composition need not be currently suffering from one or more cognition-associated diseases. For example, the subject may be a healthy subject that is not currently showing any discernible symptoms of any form of a cognitive disease, such as AD.

In one aspect of the invention, the methods of enhancing cognitive function treats and/or prevents at least some symptoms and/or pathologies associated with cognitive function decline (e.g., age-related memory decline) in the subject, regardless of the cause of the cognitive function decline. Thus in some aspects, methods of the invention provides neuroprotection. In another aspect of the invention, the methods of enhancing cognitive function enhance memory, for example, by treating memory loss or enhancing memory performance in the subject, for example, short-term memory performance or spatial reference memory performance.

Although long-term memory deficits are the hallmark of AD, deficits in short-term memory of information as well as higher level deficits (for example, deficits in the ability to evaluate, analyze, or synthesize concepts, to think critically, and to problem solve) in AD patients result in these patients' diminished ability to coordinate multiple tasks or to inhibit irrelevant information. Short-term memory is also referred to as working memory, primary memory, immediate memory, operant memory, or provisional memory. Short-term/working memory tasks are those that require the goal-oriented active monitoring or manipulation of information or behaviors in the face of interfering processes and distractions. Working memory can be divided into separate systems for retaining location information and object information (colors, shapes), which are commonly referred to as spatial working memory (SWM) and visual (or object) working memory (VWM), respectively. In some embodiments, the methods provided improve the short-term memory. In some aspects, improvements in short-term memory alleviate impairments in dual-task performance, inhibitory ability, and set-shifting ability in the AD patient. In some aspects, improvements in short-term memory results in the ability of the AD patient to remember information over a brief period of time (in the order of seconds) and the ability to actively hold information in the mind needed to do complex tasks such as reasoning, comprehension and learning is improved. Thus in some aspects, the methods of the invention treat AD.

The invention also provides methods of modulating ROCK by administering a therapeutically effective amount of the compound of Formula I or a pharmaceutical composition comprising the compound of Formula I and/or a pharmaceutically acceptable salt thereof to a subject. In one embodiment, the methods inhibit ROCK activity in the subject. Thus altering a ratio of a phosphorylated protein to a total amount of the protein. For example, the methods decrease the ratio of phosphorylated tau (p-tau) protein to total tau protein. More specifically, in some embodiments of the invention, the compositions can be used to treat one or more diseases, conditions, or other disorders that are associated with taupathy.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease. Generally, the effectiveness of treatment is determined by comparing treated groups with non-treated groups.

The methods of the invention may further comprise selecting a subject before administering a therapeutically effective amount of the compound or composition of the invention, for example, by determining the subject's ratio of p-tau to total tau protein or by testing the subject for cognitive function decline. For these embodiments, whether the subject is administered the compound of the invention and the specific amount of the compound administered depends on the subject's ratio of p-tau to total tau protein or if the subject is suffering from cognitive function decline. For example, the subject may be administered a therapeutically effective dose for enhancing cognitive function, providing neuroprotection, or inhibiting ROCK activity in the subject when the subject's ratio of p-tau to total tau protein is equal to or below the acceptable equilibrium or when the subject does not have cognitive function decline. If the subject's p-tau to total tau ratio is above the acceptable equilibrium or if the subject is suffering from cognitive function decline, the subject would be administered another therapeutically effectively dose, for example, for treating or preventing cognitive function decline, treating Alzheimer's disease, treating taupathy, inhibiting ROCK activity, or decreasing the ratio of p-tau to total tau protein in the subject.

The methods of determining the ratio of p-tau to total tau protein in the subject are established in the art. For example, the ratio of p-tau to total tau protein of the subject may be detected by analyzing the cerebral spinal fluid of the subject. Methods of quantifying the actual amount of p-tau protein and tau-protein are also well known in the art. For example, bioassay or immunoassays can be used to quantify the amount of p-tau protein, unphosphorylated tau protein, and total tau protein.

The methods of testing the subject for cognitive function decline are also established in the art. Non-limiting examples of cognitive assessment tools are the 7-minute screener, the Abbreviated Mental Test, the 6-item Blessed Orientation-Memory-Concentration Test, the Cambridge Cognitive Examination, the Clock Drawing Test, the General Practitioner Assessment of Cognition, the Memory Impairment, the Mini-Mental State Examination, the Montreal Cognitive Assessment, the Rowland Universal Dementia Assessment, the Short and Sweet Screening Instrument, the Short Blessed Test, the St Louis Mental Status, the Short Portable Mental Status Questionnaire, the Short Test of Mental Status, and the Time and Change Test.

EXAMPLES

It should be understood that while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

1. The Compound's Effect on the Ratio of p-Tau Protein to Total Tau Protein

Thirteen different ROCK inhibitors were tested for their effect on the ratio of p-tau protein to total tau protein. Five of the ROCK inhibitors tested are known compounds (Fasudil, HA11000, H1152, Y27632, and SB77) and 8 of the compounds are novel molecules (T299, T303, T306, T343, T347, T349, T350, and T355). Each drug was tested for an $IC_{10}$ value (i.e., the dosage at which 10% of the cells are no longer viable after 120 hours). Alamar Blue was used after cells were treated with the respective compounds at various dosages to determine the $IC_{10}$ value. The compounds were applied to H4-tau cells over a 96-hour time course with 8 time points (at hours 12, 24, 36, 48, 60, 72, 84, and 96). At each time point, total cell protein was collected and p-tau protein and total tau protein was assessed using an enzyme-linked immunosorbent assay. The p-tau to total tau protein ratio at each time point for each drug was compared to the corresponding time point for cells treated with vehicle (DMSO) used to solubilize the respective compound.

Two-sided t-tests were used to determine significant changes in the p-tau protein to total tau protein ratio for each drug across the entire time course at each tested time point. Cells treated by drug were compared to cells treated to vehicle.

Of the 13 drugs test at the $IC_{10}$ dosage, only Fasudil (p=0.0004), T303 (p=0.02), T343 (p=0.009), and T350 (p=0.03) displayed a significant decrease in the p-tau protein to total tau protein ratio. All of the other tested drugs had no significant effect on the ratio (p>0.05).

Fasudil and T343, two compounds that most significantly decreased the ratio of p-tau protein to tau protein, and Y27632 and T299, two compounds that had no effect on the ratio, were validated using the dosage at which 50% of the H4-tau cells are no longer viable after 120 hours (1050 value for cell survival). The time course was repeated using 4 biological replicates over 96 hours and 10 time points (at hours 0, 6, 12, 24, 36, 48, 60, 72, 84, and 96). Total cell protein was collected at each time point and ELISAs were used to measure p-tau protein and total tau protein. In addition, RNA was isolated at each of these time points to probe the mechanism for the decrease in p-tau.

Figure 2:
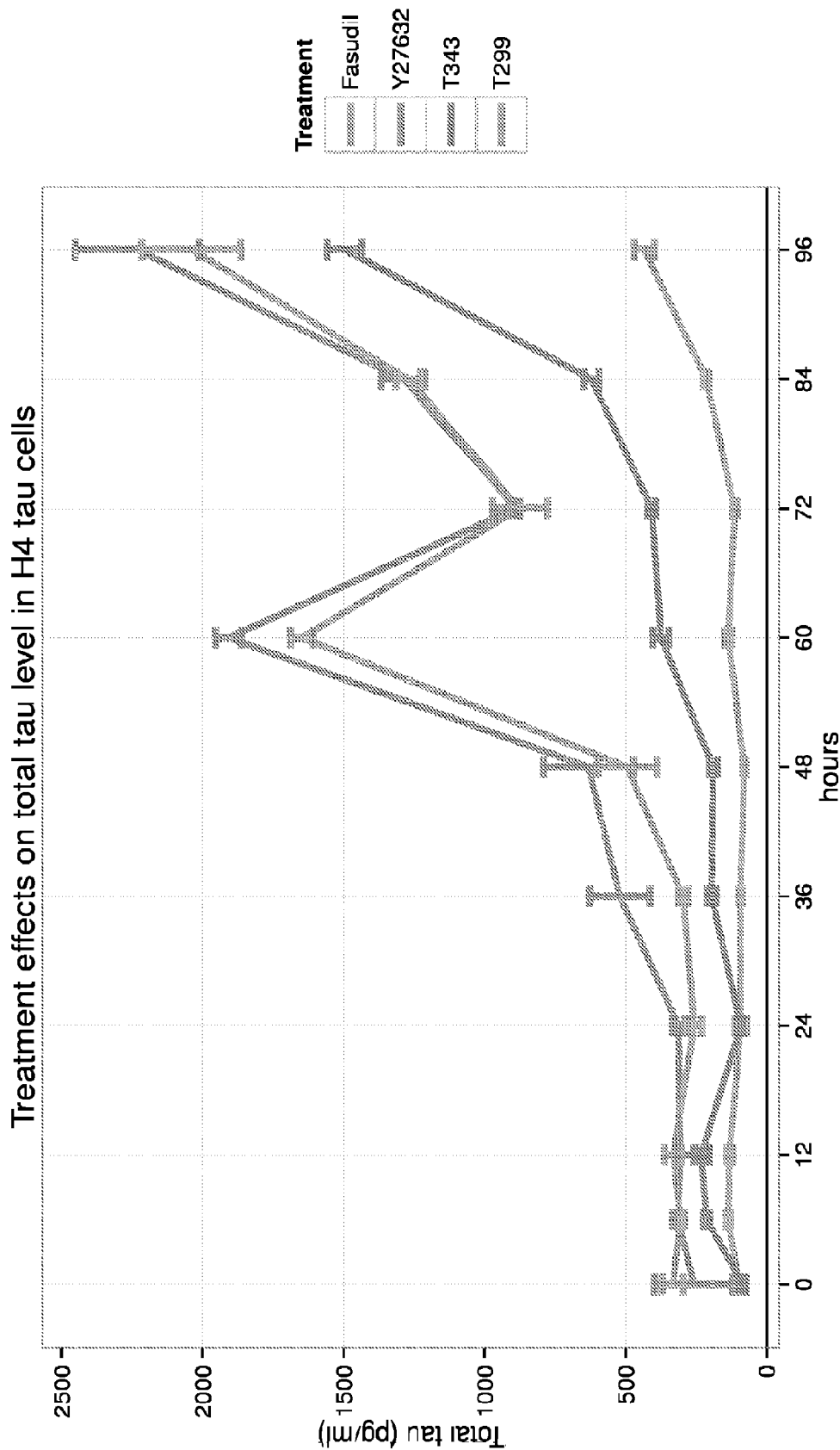
FIG. 2 is a graph depicting concentration (pg/mL) of total tau protein present in samples during a 96-hour time course experiment.
Figure 3:
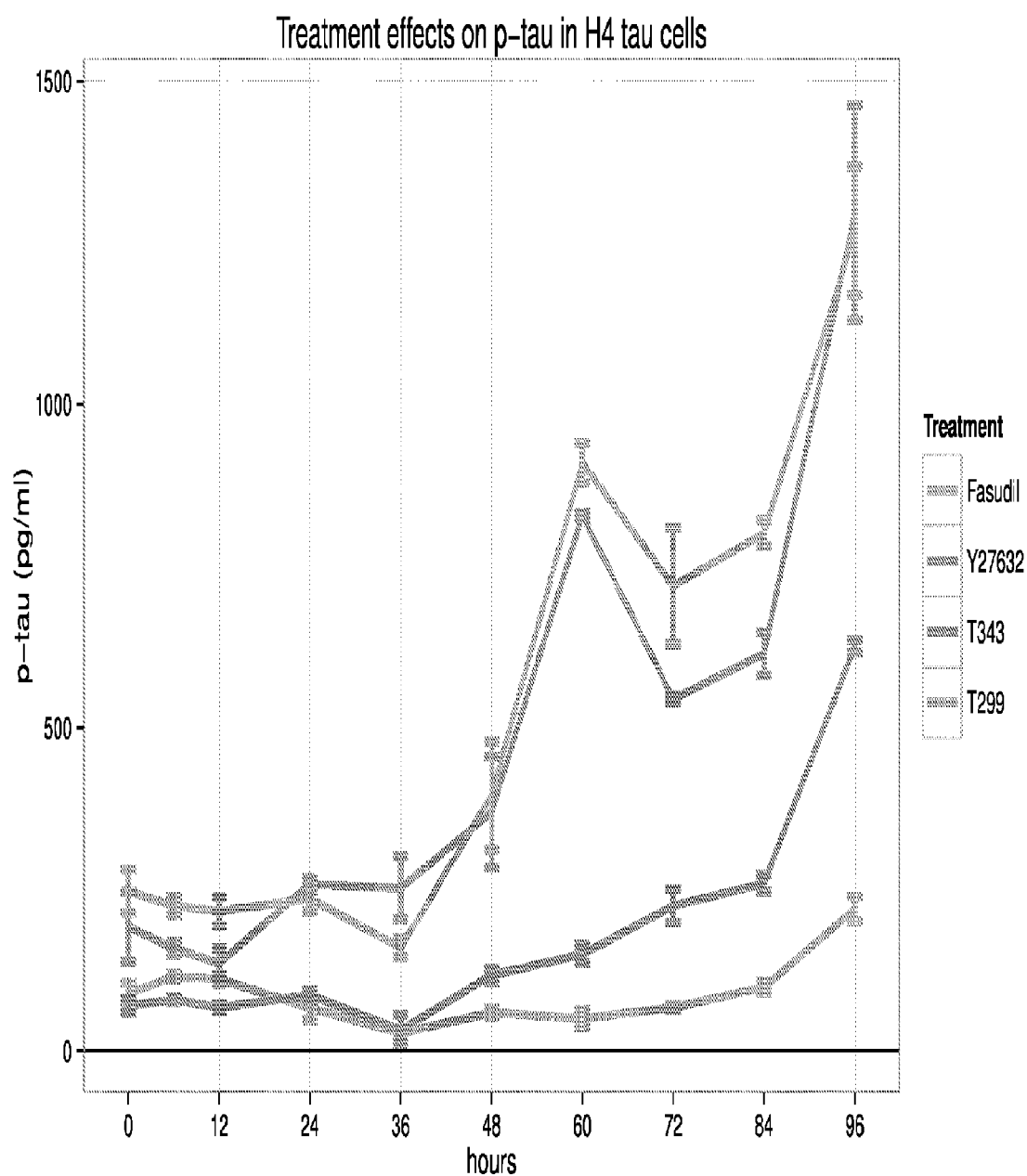
FIG. 3 is a graph depicting concentration (pg/mL) of phosphorylated tau protein present in samples during a 96-hour time course experiment.

Referring to FIG. 2, the addition of Fasudil and T343 resulted in lesser concentrations of total tau protein over the course of the experiment. Similarly, as illustrated in FIG. 3, the same phenomenon was also noted for concentrations of p-tau protein in conditions that received Fasudil and T343. In reference to FIG. 4, the ratio of p-tau protein to total tau protein was significantly decreased over the course of the experiment in conditions that received Fasudil and T343 compared to conditions that received Y27632 and T299. Fasudil and T343 were found to most significantly decrease the p-tau protein to total tau protein ratio. Fasudil induced a significant decrease in p-tau protein to total tau protein ratio beginning at 24 hours after treatment began (Fasudil: paired t(9)=−1.9, p=0.08). T343 displayed a significant decrease in the p-tau protein to total tau protein ratio from the beginning of the treatment (T343 paired t(9)=−4, p=0.003). Y27632 displayed no change at any point (paired t(9)=−2, p=0.08). T299 displayed a significant increase in the p-tau protein to total tau protein ratio from the beginning of the treatment (paired t(9)=4.8, p=0.0009).

2. Inhibition of ROCK Activity

Enzyme activity of ROCK1 and ROCK2 were studied at 10 µM to compare the inhibition activity of ROCK inhibitors. Table 2 summarizes the extent of inhibition of the compounds of the inventions.

TABLE 2

| | % enzyme activity at 10 µM | | | |
|---|---|---|---|---|
| | ROCK1 | | ROCK2 | |
| Compound | Test 1 | Test 2 | Test 1 | Test 2 |
| T299 | 0.97 | 2.38 | 0.08 | 0.15 |
| T303 | 3.26 | 2.65 | 0.78 | 0.55 |
| T306 | 6.75 | 6.94 | 3.85 | 3.62 |
| T343 | 1.22 | 1.17 | 0.08 | 0.56 |

Figure 4:
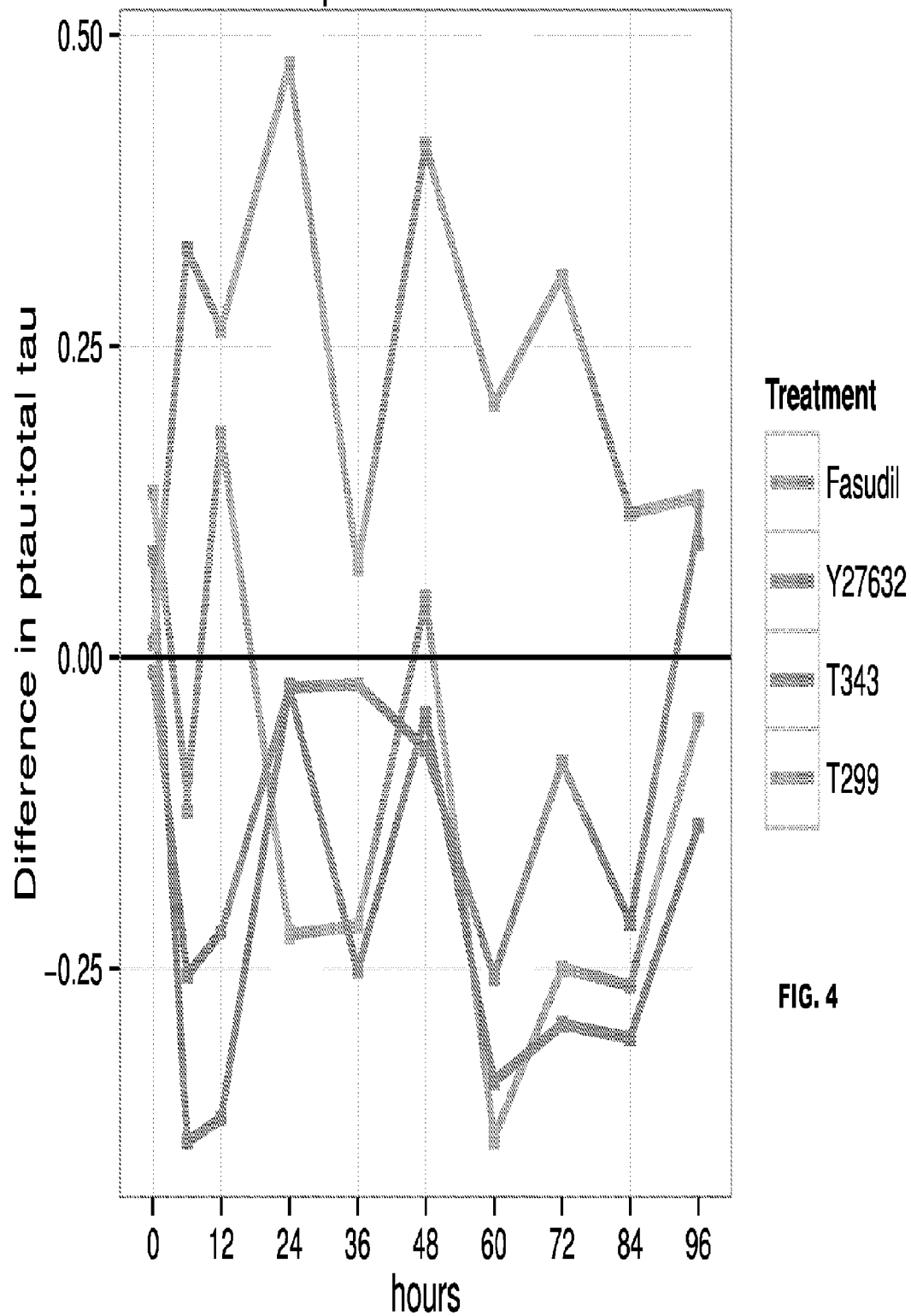
FIG. 4 is a graph depicting a ratio of concentrations of phosphorylated tau protein to total tau protein over the course of the 96-hour time course experiment of FIGS. 2 and 3.

The treatment of H4-tau cells using different ROCK inhibitors did not result in similar results in the ratio of p-tau protein to total tau protein across all drug treatments. Compounds with similar inhibition of enzyme activity, such as T299 and T343, as shown in Table 2, have different effects on the ratio of p-tau protein to total tau protein. As shown in FIG. 4, T343 resulted in decreased ratio of p-tau protein to total tau protein while T299 did not. Thus the relationship between ROCK activity and the ratio of p-tau protein to total tau protein is complex.

3. $IC_{50}$ Value for ROCK Activity

The concentration of compounds at which enzyme activity is inhibited by 50% was determined using in vitro testing against both ROCK1 and ROCK2. Briefly, replicate experiments were performed with ten, three-fold serial dilutions of the compound, with a starting concentration of 283.5 µM in at the Km value for ATP (10 µM). Similarly, the control compound, staurosporine, a known potent kinase inhibitor, was used with a starting concentration of 20 µM under the same conditions. Table 3 summarizes the $IC_{50}$ value for ROCK1 and ROCK2.

TABLE 3

| Compound | $IC_{50}$ (µM) | | | |
| --- | --- | --- | --- | --- |
| | ROCK1 | | ROCK2 | |
| | Test 1 | Test 2 | Test 1 | Test 2 |
| Fasudil | 10.7 | | 1.9 | |
| Y27632 | 0.14 | | 0.3 | |
| Stauroporine | <0.0010 | | <0.0010 | |
| T343 | 0.0318 | 0.0227 | 0.0167 | 0.0102 |

Figure 5:
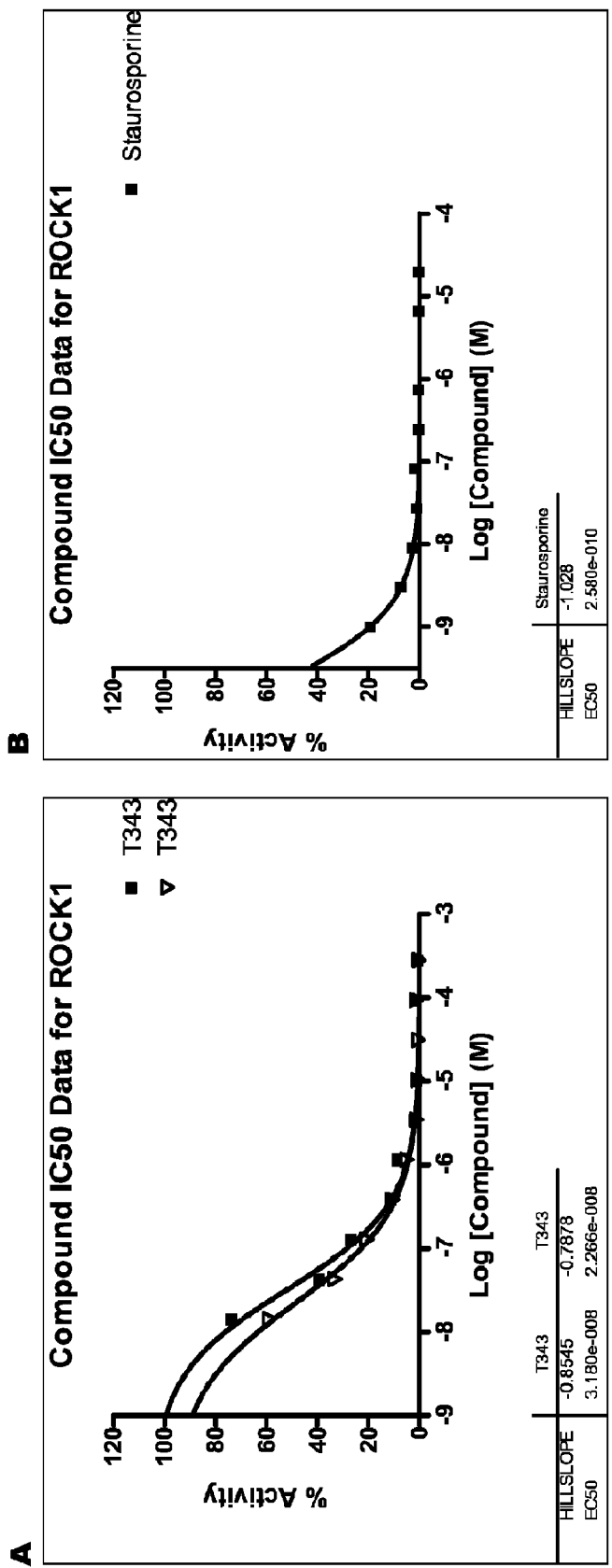
FIG. 5 is a line graph depicting inhibitory concentrations of serial dilutions of T343 (two identical replicates) (FIG. 5A) and staurosporine (FIG. 5B) on ROCK1.
Figure 6:
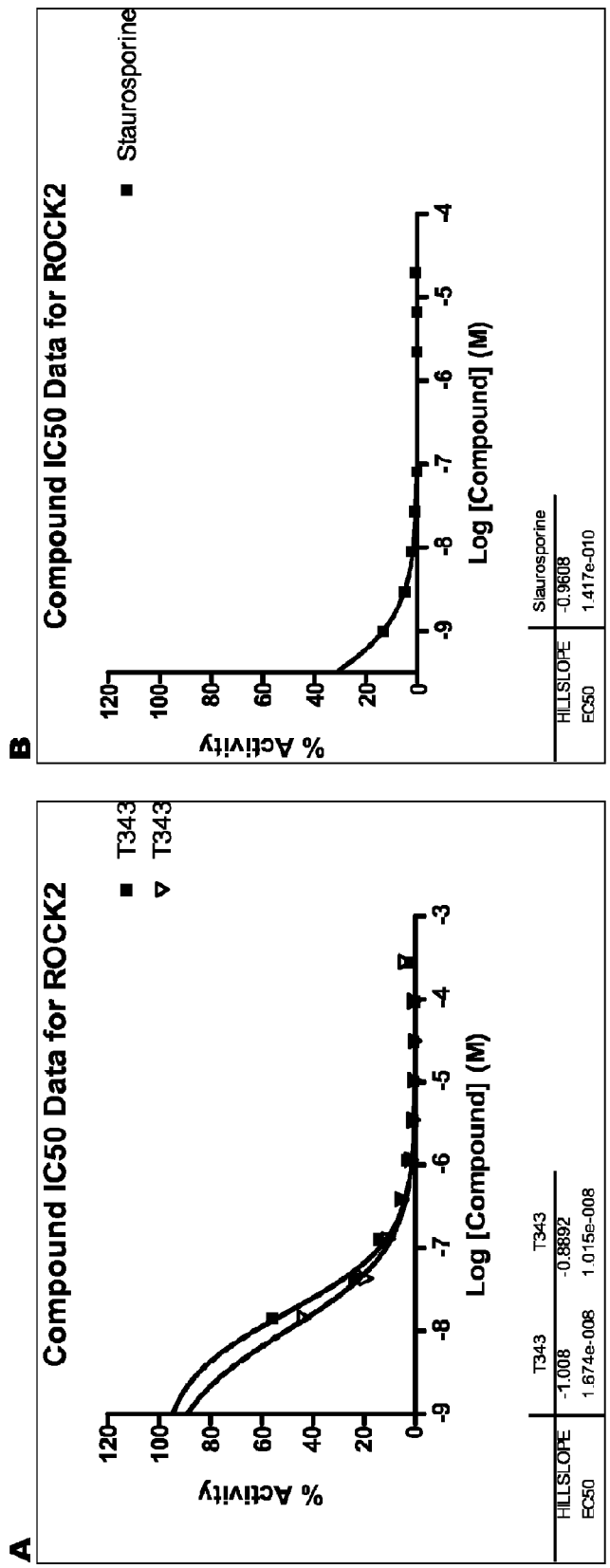
FIG. 6 is a line graph depicting inhibitory concentrations of serial dilutions of T343 (FIG. 6A) (two identical replicates) and staurosporine (FIG. 6B) on ROCK2.

Because ROCK2 is found more often in the brain and ROCK1 is mostly found in the periphery, the extent of ROCK2 kinase inhibition is more desirable to assess. As illustrated in Tables 2 and 3, Fasudil and Y27632 have more similar kinase inhibition for ROCK2 compared to ROCK1 based on their IC50 concentrations, while T343 and T299 have similar inhibition for both ROCK1 and ROCK2 based on the extent of enzyme inhibition at 10 µM. Moreover, as reflected in Table 3 and FIGS. 5 and 6, the IC50 value for T343 is of a similar magnitude to Fasudil.

What is claimed is:

1. A compound selected from the group consisting of

(Formula I)

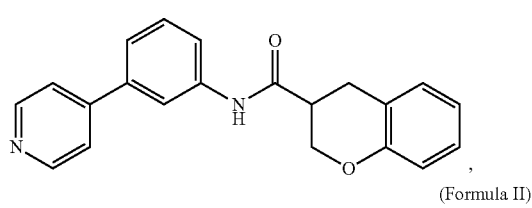

(Formula II)

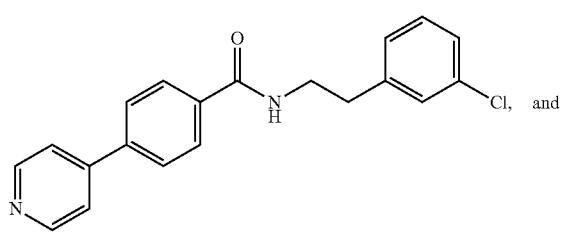

(Formula III)
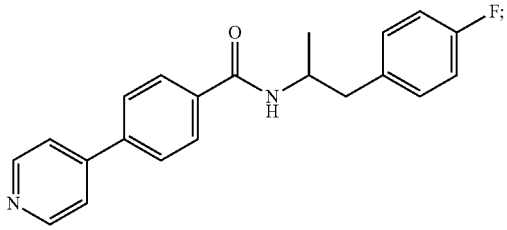

or a pharmaceutically acceptable salt or solvate thereof.

2. A pharmaceutical composition comprising a compound selected from the group consisting of:

(Formula I)
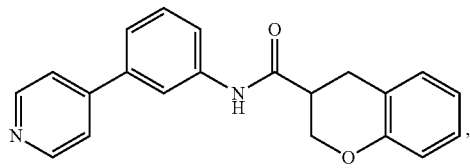

(Formula II)
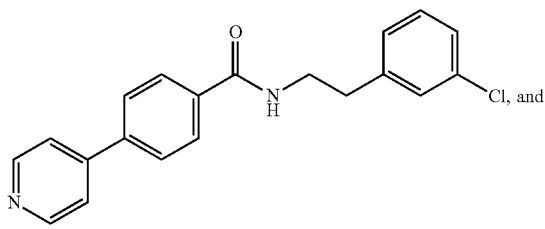

(Formula III)
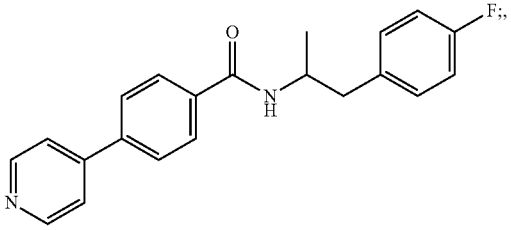

or a pharmaceutically acceptable salt or solvate thereof and a pharmaceutically acceptable carrier.

3. The pharmaceutical composition of claim 2, further comprising a therapeutically effective amount of a second effective compound, wherein the second effective compound has a different structure than the compound of claim 2.

4. A method of enhancing cognitive function in a subject in need thereof, the method comprising the step of: administering to the subject at least one compound of claim 1.

5. A method of reducing cognitive function decline in a subject in need thereof, the method comprising the step of: administering to the subject at least one compound of claim 1.

6. The method of claim 5, wherein the cognitive function is short-term memory performance.

7. The method of claim 5, wherein the cognitive function is spatial reference memory performance.

8. The method of claim 5, wherein the cognitive function decline results from Alzheimer's disease.

* * * * *